(12) United States Patent
Björn et al.

(10) Patent No.: US 6,896,517 B1
(45) Date of Patent: May 24, 2005

(54) SELF-TAPPING IMPLANT

(75) Inventors: Göran Björn, Onsala (SE); Fredrik Engman, Molnlycke (SE); Lars Jörnéus, Frillesás (SE)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/936,169
(22) PCT Filed: Feb. 23, 2000
(86) PCT No.: PCT/SE00/00351

§ 371 (c)(1),
(2), (4) Date: Dec. 26, 2001

(87) PCT Pub. No.: WO00/53117

PCT Pub. Date: Sep. 14, 2000

(30) Foreign Application Priority Data

Mar. 9, 1999 (SE) .................................... 9900822

(51) Int. Cl.$^7$ ................................................ A61C 8/00
(52) U.S. Cl. ...................................... 433/174; 433/173
(58) Field of Search ............................... 433/174, 172, 433/173, 175; 606/61, 65, 72; 623/16.11, 623/11.11, 23.5

(56) References Cited

U.S. PATENT DOCUMENTS 5,727,943 A * 3/1998 Beaty et al. ................. 433/174
5,897,319 A * 4/1999 Wagner et al. .............. 433/174

FOREIGN PATENT DOCUMENTS

| EP | 0641549 A2 | 3/1995 |
| WO | WO 9703621 A1 | 2/1997 |
| WO | WO 9743976 A1 | 11/1997 |

* cited by examiner

Primary Examiner—Cary E. O'Connor
Assistant Examiner—Candice C. Stokes
(74) Attorney, Agent, or Firm—Connolly Bove Lodge & Hutz LLP; Larry J. Hume

(57) ABSTRACT

A self-tapping implant for jawbone comprises a body (15) with threads arranged thereon, a conically tapering portion (12) arranged at its front end, and one or more spaces (4, 5, 6) which accommodate bone material cut off during tapping and which are formed by removal of material from the threads and body in question. Each materially reduced thread has a cutting edge (1a, 2a, 3a) which extends inwards from the outer edge of the respective remaining thread part and which can cooperate with the bone during tapping. Each cutting edge of a number of cutting edges has a pointed shape (1b, 2b, 3b) which, in the cross section of the thread in question, essentially follows a line which deviates from a radius (r) through the remaining thread part's front portion or the pointed shape's point (1b, 2b, 3b) in order in this way to form a cutting angle. Each cutting edge (1a, 2a, 3a) on a first remaining thread part (1, 2, 3) merges via a radius (r') or curved part into a rear edge (e.g. 2d) on a second remaining thread part, which is arranged before the first thread part in the direction of screwing (7), for the purpose of providing optimum remaining material in the body and remaining thread parts and, consequently, optimum strength of the implant part in question.

5 Claims, 2 Drawing Sheets

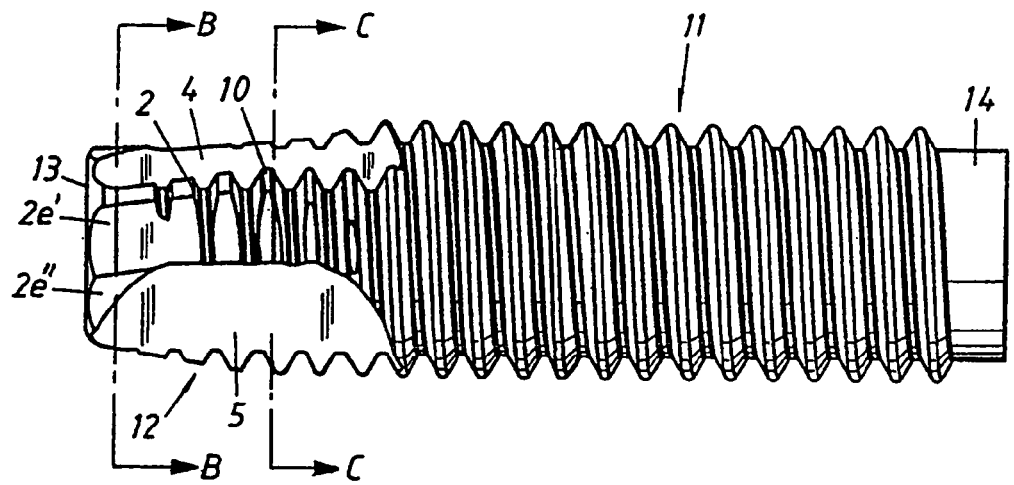
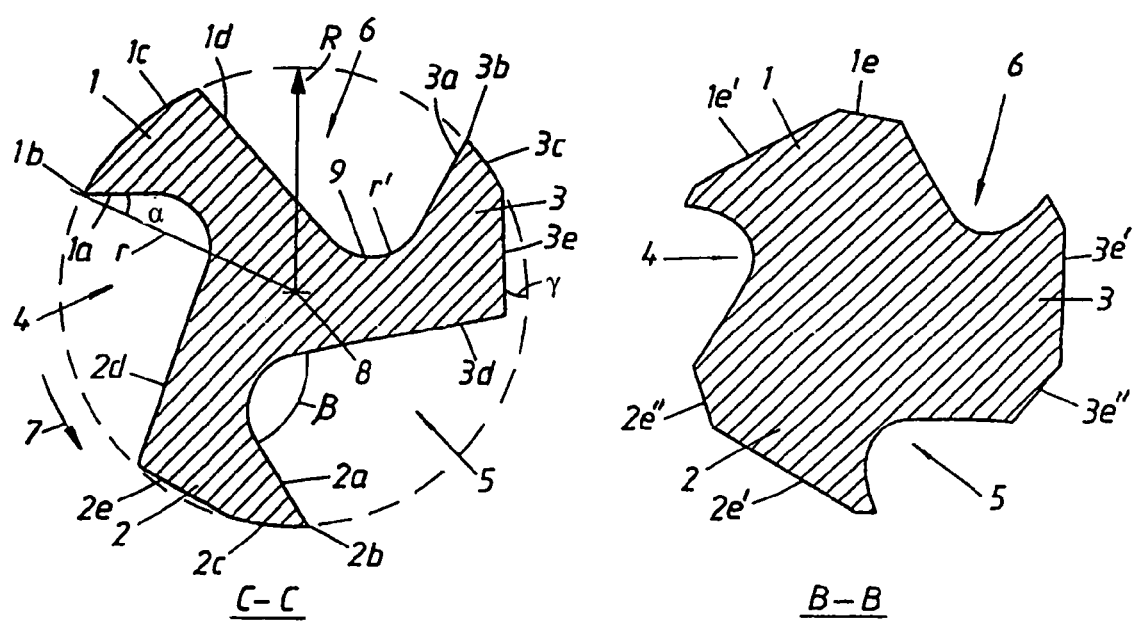

A-A

SELF-TAPPING IMPLANT

CROSS-REFERENCE TO RELATED APPLICATIONS

This application is a National Stage Entry under 35 U.S.C. §371 of International Application PCT/SE0000351, filed on Feb. 23, 2000, and which claims priority to Swedish Application number 9900822-9, filed Mar. 9, 1999, the entire contents of each of which are incorporated herein by reference.

TECHNICAL FIELD

The present invention relates to a self-tapping implant for bone, preferably jawbone. The implant comprises a body with threads arranged thereon, and a conically tapering portion arranged at its front end. In addition, there are one or more spaces, here called bone-chip recesses, which accommodate bone material cut off during tapping and which are formed by removal of material from the threads and body in question. Each materially reduced thread has a cutting edge which extends inwards from the outer edge of the respective remaining part and which cooperates with the bone/jawbone during tapping.

PRIOR ART

Self-tapping dental implants are already well known. A characteristic of many implant types is that they have a relatively dense threading. There are also implants with relatively sparse threading. It is also known to provide implants with multiple threads, for example double threads, by which means the speed of screwing can be increased. In principle, the thread configurations used aim to make it easier to screw the implants into jawbone or other bone in the human body, and to provide initial anchoring of the implant in the bone. Reference is made, inter alia, to Swedish patent 9601913-8, which discloses an implant with a conically tapering front end and with spaces or bone-chip recesses provided for bone material that has been cut off. Reference is also made to EP 0 641 549 which shows that it is already known per se to use multiple threads on implants.

DESCRIPTION OF THE INVENTION

Technical Problem

There is a general need to provide good cutting characteristics on the implant so that the latter can be fitted without preliminary threading, which means, among other things, that the implant has to be designed with a thread-cutting point which is formed with a special cutting geometry. The invention aims to solve this problem among others.

In connection with the design of the implant, the aim is to avoid using a dense threading, as this entails a low insertion speed. Nor is a sparse threading wanted, as this entails small thread surfaces in contact with the bone tissue and, consequently, poor conditions for successful osseointegration. If the thread is given a deep profile, it is possible to compensate for this, but at the expense of the implant's strength. The use of double threads is not completely free of problems either in this context, since a double thread, at each moment of insertion, must cut away twice as much bone, which means that the double-threaded implant meets considerably greater resistance from the bone. Theoretically, the cutting resistance is approximately twice as great. During insertion, frictional forces also have the effect that the total resistance can be about 50% higher compared to the case of a corresponding implant geometry with a single thread. For this reason, double-threaded implants are advantageously used mainly in soft bone. The use of double-threaded implants in hard bone entails high insertion resistance from the bone. An implant can always be fitted using a thread tap, but a double-threaded design does not then represent any simplification or saving in time. The present invention also solves this problem and discloses a novel approach in which the implant is provided with excellent cutting characteristics which mean that it can be fitted without preliminary threading in the bone or jawbone in question.

In these types of implants, there is a further requirement that the implant must be designed with sufficient strength. This is especially important in hard bone, where the resistance to the screwing-in function can be considerable. The need for considerable or sufficient strength is often in conflict with the need for a suitable cutting geometry or thread design. The invention solves this problem too.

Solution

The novel approach disclosed by the invention entails, inter alia, that the thread-cutting point of the implant is designed with a special cutting geometry which in embodiments is combined with features known per se, and these, taken together, afford an especially advantageous threading function for the self-tapping implant.

The feature which can principally be regarded as characterizing an implant according to the invention is that each cutting edge of a number, preferably all, of the cutting edges of the removed threads have a pointed shape which, in the cross section of the thread in question, essentially follows a line which deviates from a radius through the remaining thread part's front portion or the pointed shape's point. The cutting angle or chip angle formed by the pointed shape is chosen so as to give an effective threading property which is in relation to the threading property of the implant, i.e. ensures sufficient remaining materially-reduced thread and body. The relationship between cutting properties and strength is preferably optimal.

In a preferred embodiment, the cutting angle or chip angle is about 20° and is chosen preferably within a range of 15–40°. The said refinements can also include the cutting edge on a first remaining thread part merging via a radius or curved part into a rear edge on a second remaining thread part, which lies before the first thread part in the direction of screwing of the implant. The radius or the curved part is in this case arranged to provide optimum remaining material in the body and remaining thread part or thread parts and, consequently, optimum strength of the implant in question.

The conically tapering portion or tip of the implant must be arranged to support at least two thread parts which extend out to the full radial dimension of the thread in question. The point angle of the cone-shaped portion or cone-shaped implant tip is preferably less than about 20°. A thread relief which is to be effected by removed or materially reduced thread parts is preferably arranged on the conically tapering portion or the point in order to reduce or minimize clamping tendencies between the implant and the bone tissue during threading. The bone chip cutting edge is also preferably arranged non-axially. One or more remaining thread parts on one or more threads are provided with material reduction behind, as viewed in the direction of screwing, the full diameter part which can be engaged with the bone or the bone tissue, for the purpose of facilitating the relief function upon threading.

Advantages

By means of what has been proposed above, an excellent screwing function is obtained for implants in dentine or other bone types. The design of the specific cutting edges and the remaining thread part and the connection of this to the body guarantee good strength of the implant, and at the same time a sufficiently large threaded periphery is obtained for the implant. This geometry of the bone-chip recesses, cutting edges and body can be obtained by milling with a so-called dovetail cutter which has rounded corners. The bone-chip recesses can be given adequate volume, i.e. the volume can be made so great that the detached bone is accommodated without excessive compression, which can give rise to friction between fixture and surrounding bone tissue upon insertion or screwing. The design also means that clamping tendencies between the fixture/implant and the bone tissue can be minimized.

DESCRIPTION OF THE FIGURES

A presently proposed embodiment of an implant according to the invention will be described below with reference to the attached drawings, in which:

FIG. 1 shows a side view of the implant,

FIG. 2 shows, in two cross sections B—B and C—C, a thread with reduced material or with material removed, and its remaining thread parts and specific cutting edge arrangement.

DETAILED EMBODIMENT

Figure 3:
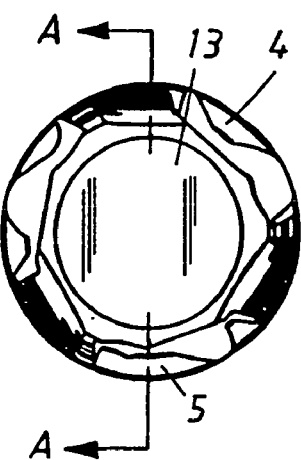
FIG. 3 shows an end view of the implant according to FIG. 1.

FIG. 1 shows a side view of an implant which has a cylindrical threaded part and a front, cone-shaped portion with materially reduced threads. FIG. 2 shows the cross sections B—B and C—C through the materially reduced threads according to FIG. 1. According to FIG. 2 and the cross section C—C, a thread with material reduction or material removed is shown with its remaining thread parts 1, 2 or 3 which in this case are three in number. Between the thread parts there are spaces 4, 5, 6 which accommodate detached bone tissue. In this illustrative embodiment, the thread parts and the spaces are essentially uniformly distributed about the circumference of the implant. Another pattern of distribution and another number of spaces are possible. The circumferential direction of the implant is indicated by 7 and the implant axis at right angles to the plane of the figure is indicated by 8.

The thread parts are provided with cutting edges 1a, 2a and 3a which cooperate with or cut into bone tissue when the implant is being threaded into the bone in the circumferential direction 7. A characteristic feature of the cutting function is that the cutting edges are designed with points or parts 1b, 2b, 3b. The thread parts also have parts 1c, 2c and 3c which extend along the full radius R or along the circumferential direction 7 and which define the thread diameter in the bone produced with the thread in question. The rear sides of the thread parts are indicated by 1d, 2d and 3d.

To form a cutting edge with cutting angle (or chip angle) α, the cutting edge extends in relation to the actual radius r at the said angle α which can be chosen at about 20° or within the range of 15–40°. At its inner parts, the cutting edge on a first thread part, for example thread part 3, merges into the rear side, for example the rear side 1d, of an adjoining thread part, for example thread part 1, via a radius-shaped or curved transition part 9 which has a certain length at right angles to the plane of the figure. A radius for the curved part is indicated by r'. One or more of the remaining thread parts can have a relief edge 2e, 3e, behind its circular part 2c and 3c, respectively.

FIG. 2 shows an angle β between cutting and rear edges of successive thread parts, as viewed in the direction of rotation 7. In this illustrative embodiment, the angle ° must be about 70°, and it can be of the same size or different sizes. A relief angle γ between the circular part 3c and the relief surface 3e is chosen at 5–10°.

In FIG. 1, the reduced thread shown in cross section in FIG. 1 is indicated by 10. The positions of the spaces 4 and 5 can also be seen, the remaining thread part between these two spaces being indicated by 2. The implant or the fixture has a cylindrical part 11 with non-reduced threads and a front cone-shaped portion 12 with materially reduced threads. The impressions or recesses have been formed by material reduction in the said threads and in the body of the implant. The free end of the implant, which is essentially straight and chosen at right angles in relation to the longitudinal axis of the implant, is indicated by 13. The upper part of the implant is indicated by 14. As can be seen from the figure, the relief edge 2e of the remaining thread part 2 consists of two essentially plane relief surfaces 2e' and 2e", which form an obtuse angle with each other. This is best seen from the cross section B—B in FIG. 2, where respective relief surfaces have been indicated.

In the end view in FIG. 3, the surface 13 and the lower edge of the spaces 4 and 5 are shown. A longitudinal section A—A through the longitudinal axis of the implant is shown in FIG. 4 below.

Figure 4:
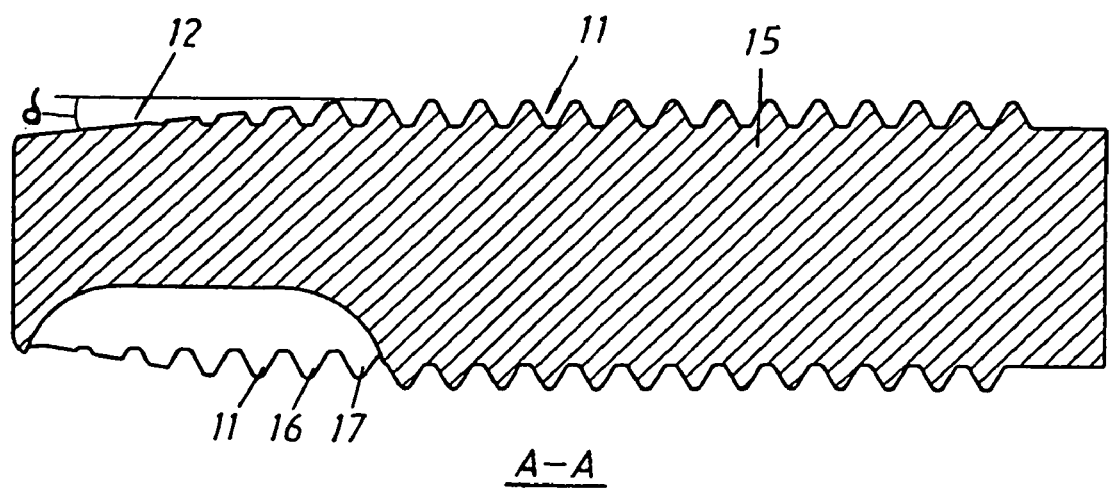
FIG. 4 shows the longitudinal section A—A according to FIG. 3.

In FIG. 4, the body of the implant is indicated by 15. The cone-shaped portion (or point) 12 is designed with a point angle δ which in this case is up to about 10°. The bone-chip recesses or spaces 4, 5 and 6 (see also FIG. 1) are located in the cone-shaped portion 12 and continue partially into the cylindrical portion. By means of the above, non-axially arranged cutting edges are obtained via the reduced threads overlying one another. A materially reduced thread must have at least one thread part, preferably at least two thread parts, with cutting edges which reach the circumference of the thread in question. On the cone-shape portion 12, the cutting edge in this case has three thread parts 11, 16, 17 which extend to the full radius, for example r in FIG. 1. For other lengths, the number of thread parts can be reduced or increased, but it needs to be at least one.

The implant can be provided with one, two or more thread leads or spirals. The spirals can extend wholly or partly in the vertical direction of the implant, i.e. one part, for example 14, can be provided with a double-thread or multiple-thread arrangement, and a part, for example 13, can be provided with a single-thread arrangement or a thread arrangement with different thread number, or vice versa.

The invention is not limited to the embodiment shown above by way of example, but can be modified within the scope of the attached patent claims and the inventive concept.

What is claimed is:

1. A self-tapping implant for use in a bone, preferably a jawbone, the implant comprising:
   a body with plural threads arranged thereon,
   a conically tapering portion arranged at a front end of the body and having one or more bone-chip recesses therein which accommodate bone material cut off during a tapping operation,
   said one or more bone-chip recesses being formed by removal of material from the plural threads and body,
   wherein, at least in the conically tapering portion, the plural threads are materially reduced, each of the materially reduced threads having a cutting edge which extends inward from an outer edge of a respective remaining thread part,
   said respective remaining thread part cooperatively engaging with the bone during the tapping operation,
   wherein each cutting edge of a number of associated cutting edges of the materially reduced threads have a pointed shape which, in a cross section thereof, essentially follows a line which deviates from a first radius through a point of the pointed shape of the respective remaining thread part,
   wherein a cutting edge on a first remaining thread part merges via a second radius into a rear edge on a second remaining thread part arranged before the first thread part in an implant screwing direction,
   said cutting edge on the first remaining part being selected to provide an effective threading characteristic with respect to a desired strength of the implant,
   wherein a cutting angle formed by the pointed shape is selected to be within a range of between 15–40°,
   wherein each of plural thread relief edges effected by a respective one of the materially reduced thread parts is arranged essentially in the conically tapering portion and behind, as viewed in the implant screwing direction,
   wherein full radius portions of the two or more plural thread spirals within the conically tapering portion are engaged with the bone to provide a threading relief function during the tapping operation,
   wherein the self-tapping implant comprises multiple thread spirals along at least a portion of a length thereof,
   wherein a first portion is provided with multiple threads, and a second portion is provided with a single thread or thread numbering different from a thread numbering of the first portion.

2. A self-tapping implant for use in a bone, preferably a jawbone, the implant comprising:
   a body with plural threads arranged thereon;
   a conically tapering portion arranged at a front end of the body and having one or more bone-chip recesses therein which accommodate bone material cut off during a tapping operation,
   said one or more bone-chip recesses being formed by removal of material from the plural threads and body,
   wherein, at least in the conically tapering portion, the plural threads are materially reduced, each of the materially reduced threads having a cutting edge which extends inward from an outer edge of a respective remaining thread part,
   said respective remaining thread part cooperatively engaging with the bone during the tapping operation,
   wherein each cutting edge of a number of associated cutting edges of the materially reduced threads have a pointed shape which, in a cross section thereof, essentially follows a line which deviates from a first radius through a point of the pointed shape of the respective remaining thread part,
   wherein a cutting edge on a first remaining thread part merges via a second radius into a rear edge on a second remaining thread part arranged before the first thread part in an implant screwing direction,
   said cutting edge on the first remaining part being selected to provide an effective threading characteristic with respect to a desired strength of the implant,
   wherein a cutting angle formed by the pointed shape is selected to be about 20°,
   wherein each of plural thread relief edges effected by a respective one of the materially reduced thread parts is arranged essentially in the conically tapering portion and behind, as viewed in the implant screwing direction,
   wherein full radius portions of the plural threads within the conically tapering portion are engaged with the bone to provide a threading relief function during the tapping operation,
   wherein the self-tapping implant comprises multiple threads along at least a portion of a length thereof,
   wherein a first portion is provided with a multiple thread, and a second portion is provided with a single thread or thread numbering different from a thread numbering of the first portion.

3. A self-tapping implant for use in a bone, preferably a jawbone, the implant comprising:
   a body with plural threads arranged thereon;
   a conically tapering portion arranged at a front end of the body and having one or more bone-chip recesses therein which accommodate bone material cut off during a tapping operation,
   said one or more bone-chip recesses being formed by removal of material from the plural threads and body,
   wherein, at least in the conically tapering portion, the plural threads are materially reduced, each of the materially reduced threads having a cutting edge which extends inward from an outer edge of a respective remaining thread part,
   said respective remaining thread part cooperatively engaging with the bone during the tapping operation,
   wherein each cutting edge of a number of associated cutting edges of the materially reduced threads have a pointed shape which, in a cross section thereof, essentially follows a line which deviates from a first radius through a point of the pointed shape of the respective remaining thread part,
   wherein a cutting edge on a first remaining thread part merges via a second radius into a rear edge on a second remaining thread part arranged before the first thread part in an implant screwing direction,
   said cutting edge on the first remaining part being selected to provide an effective threading characteristic with respect to a desired strength of the implant,
   wherein a cutting angle formed by the pointed shape is selected to be within a range of between 15–40°,
   wherein each of plural thread relief edges effected by a respective one of the materially reduced thread parts is arranged essentially in the conically tapering portion and behind, as viewed in the implant screwing direction,
   wherein full radius portions of the plural threads within the conically tapering portion are engaged with the bone to provide a threading relief function during the tapping operation, wherein the self-tapping implant comprises multiple threads along at least a portion of a length thereof, wherein the conically tapering portion is arranged with materially reduced thread parts with full radius and which are at least two in number, wherein a first portion is provided with a multiple thread, and a second portion is provided with a single thread or thread numbering different from a thread numbering of the first portion.

4. A self-tapping implant for use in a bone, preferably a jawbone, the implant comprising:

a body with plural threads arranged thereon;

a conically tapering portion arranged at a front end of the body and having one or more bone-chip recesses therein which accommodate bone material cut off during a tapping operation, said one or more bone-chip recesses being formed by removal of material from the plural threads and body, wherein, at least in the conically tapering portion, the plural threads are materially reduced, each of the materially reduced threads having a cutting edge which extends inward from an outer edge of a respective remaining thread part, said respective remaining thread part cooperatively engaging with the bone during the tapping operation, wherein each cutting edge of a number of associated cutting edges of the materially reduced threads have a pointed shape which, in a cross section thereof, essentially follows a line which deviates from a first radius through a point of the pointed shape of the respective remaining thread part, wherein a cutting edge on a first remaining thread part merges via a second radius into a rear edge on a second remaining thread part arranged before the first thread part in an implant screwing direction, said cutting edge on the first remaining part being selected to provide an effective threading characteristic with respect to a desired strength of the implant, wherein a cutting angle formed by the pointed shape is selected to be less than 20°, wherein each of plural thread relief edges effected by a respective one of the materially reduced thread parts is arranged essentially in the conically tapering portion and behind, as viewed in the implant screwing direction, wherein full radius portions of the plural threads within the conically tapering portion are engaged with the bone to provide a threading relief function during the tapping operation, wherein the self-tapping implant comprises multiple threads along at least a portion of a length thereof, wherein a first portion is provided with a multiple thread, and a second portion is provided with a single thread or thread numbering different from a thread numbering of the first portion.

5. A self-tapping implant for use in a bone, preferably a jawbone, the implant comprising:

a body with plural threads arranged thereon;

a conically tapering portion arranged at a front end of the body and having one or more bone-chip recesses therein which accommodate bone material cut off during a tapping operation, said one or more bone-chip recesses being formed by removal of material from the plural threads and body, wherein, at least in the conically tapering portion, the plural threads are materially reduced, each of the materially reduced threads having a cutting edge which extends inward from an outer edge of a respective remaining thread part, said respective remaining thread pan cooperatively engaging with the bone during the tapping operation, wherein each cutting edge of a number of associated cutting edges of the materially reduced threads have a pointed shape which, in a cross section thereof, essentially follows a line which deviates from a first radius through a point of the pointed shape of the respective remaining thread part, wherein a cutting edge on a first remaining thread part merges via a second radius into a rear edge on a second remaining thread part arranged before the first thread part in an implant screwing direction, said cutting edge on the first remaining part being selected to provide an effective threading characteristic with respect to a desired strength of the implant, wherein a cutting angle formed by the pointed shape is selected to be within a range of between 15–40°, wherein each of plural thread relief edges effected by a respective one of the materially reduced thread parts is arranged essentially in the conically tapering portion and behind, as viewed in the implant screwing direction, wherein full radius portions of the plural threads within the conically tapering portion are engaged with the bone to provide a threading relief function during the tapping operation, wherein the self-tapping implant comprises multiple threads along at least a portion of a length thereof, wherein each relief edge comprises two essentially plane relief surfaces which form an obtuse angle with respect to each other, wherein a first portion is provided with a multiple thread, and a second portion is provided with a single thread or thread numbering different from a thread numbering of the first portion.

* * * * *